US006936271B1

(12) United States Patent
Oliver et al.

(10) Patent No.: US 6,936,271 B1
(45) Date of Patent: Aug. 30, 2005

(54) COLLAGENOUS TISSUE COMPOSITIONS

(75) Inventors: Roy Oliver, Scotland (GB); Roy Grant, Dorset (GB)

(73) Assignee: Tissue Science Laboratories PLC, Hampshire (GB)

( * ) Notice: Subject to any disclaimer, the term of this patent is extended or adjusted under 35 U.S.C. 154(b) by 0 days.

(21) Appl. No.: 09/786,853

(22) PCT Filed: Sep. 10, 1999

(86) PCT No.: PCT/GB99/03013

§ 371 (c)(1),
(2), (4) Date: Jul. 2, 2001

(87) PCT Pub. No.: WO00/15274

PCT Pub. Date: Mar. 23, 2000

(30) Foreign Application Priority Data

Sep. 11, 1998 (GB) .................................. 9819882

(51) Int. Cl.[7] .......................... A61F 2/02; A61F 2/28; A61K 9/14; A61K 9/50
(52) U.S. Cl. ...................... 424/426; 424/489; 424/499; 523/113; 523/114
(58) Field of Search ............................. 424/499, 422, 424/423, 489, 484, 426; 523/113, 114

(56) References Cited

U.S. PATENT DOCUMENTS

| | | | | |
|---|---|---|---|---|
| 4,582,640 A | * | 4/1986 | Smestad et al. ............ 260/123 |
| 4,803,075 A | | 2/1989 | Wallace et al. ............. 424/423 |
| 4,837,285 A | * | 6/1989 | Berg et al. .................. 530/356 |
| 5,256,140 A | * | 10/1993 | Fallick ......................... 604/51 |
| 5,397,353 A | * | 3/1995 | Oliver et al. ................. 623/11 |
| 5,523,291 A | * | 6/1996 | Janzen et al. ................ 514/21 |
| 5,658,593 A | * | 8/1997 | Orly et al. ................... 424/499 |
| 5,705,488 A | | 1/1998 | Janzen et al. ................ 514/21 |

FOREIGN PATENT DOCUMENTS

| | | | |
|---|---|---|---|
| EP | 0 083 868 | | 7/1983 |
| EP | 0083868 B1 | * | 4/1986 |
| EP | 0 251 695 | | 1/1988 |
| EP | 0251695 A2 | * | 1/1988 |
| EP | 0 697 218 | | 2/1996 |
| EP | 0697218 A2 | * | 2/1996 |
| EP | 0747067 A2 | * | 11/1996 |
| WO | WO 93/13755 | * | 7/1993 |
| WO | WO 00/15274 | * | 3/2000 |

* cited by examiner

Primary Examiner—Carlos A. Azpuru
(74) Attorney, Agent, or Firm—Hogan & Hartson LLP

(57) ABSTRACT

Implant compositions are disclosed consisting of a biocompatible carrier medium such as a saline or dextran solution and particles of collagenous material dispersed therein. The collagenous material is derived from tissue which has been milled to provide fragments of collagen fibers which preserve the architecture of the original fibers and their molecular structure. The collagenous material is also substantially free of non-fibrous tissue proteins, glycoproteins, cellular elements and lipids or lipid residues, and is non-cytotoxic. By suitable choice of particle size and concentration, the composition may be presented in injectable form or as a paste. The compositions are suitable for application in cosmetic and reconstruction surgery.

13 Claims, No Drawings

COLLAGENOUS TISSUE COMPOSITIONS

This invention relates to collagenous tissue compositions.

In recent years, much attention has been given to the development of compositions and preparations for wound treatment and for use in general and plastic surgery, in particular for the improved restoration of surgically induced wounds or for the correction of physiological malfunction as, for example, of the urethral sphincter in cases of urinary incontinence.

Much attention has been focussed on the provision of materials based on collagen, either of human or animal origin. In particular, considerable attention has been directed to developing preparations and materials based on animal tissues which are treated to provide compatibility, i.e. to avoid rejection of the tissues when used on humans.

Earlier work by the inventors of the present application is reflected in U.S. Pat. No. 5,397,353 and EP-A-182842 which disclose methods of preparing collagenous materials, preferably in sheet form, and which are suitable for transplantation. The treatment is designed to produce a collagenous material which is non-antigenic so that it is not rejected and which is non-resorbable so that it forms a permanent transplant. In particular, the material described in these specifications retains the natural structure and original architecture of the natural tissue; the molecular ultrastructure of the collagen is retained. These materials have proved highly satisfactory in practice and, in particular, have shown themselves to be capable of being re-vascularised once implanted while, at the same time, being resistant to calcification. They are particularly useful in ear, nose and throat, orthopaedic, gynaecological and urological procedures and a range of hernia repairs including parastomal incisional and inguinal hernias.

The compositions described in U.S. Pat. No. 5,397,353, however, are disclosed as large scale structures, for example 0.75 mm thick and usually presented as sheets varying in size from 25 $cm^2$ to 50 $cm^2$. This is useful for specific implant use, e.g. during restorative surgery, but is not always suited for use generally to build up soft tissues.

In cosmetic and reconstructive surgery, e.g. for the repair of small acne scars and for elevating and smoothing wrinkles, it is often desirable to use material in another form for tissue implantation or so-called augmentation which can be injected or otherwise introduced into the desired site.

Various so-called injectable implant materials have been developed for such purposes. U.S. Pat. Nos. 5,523,291, 5,676,698 and 5,705,488 disclose injectable implant compositions for soft tissue augmentation comprising elastin and collagen and a biocompatible carrier, or flexible pouches containing such a material. The difficulty with such materials as are disclosed in these United States specifications, however, is that there is a tendency to resorption and this can mean that the implant is effective only for a limited time. Additionally, such materials do not encourage vascularisation, i.e. they do not integrate well into the surrounding healthy tissue following implantation.

Furthermore, in wound surgery, e.g. for repairing bullet wounds or injuries caused by machinery or vehicle accidents and indeed following incisional injury, there is often a problem in that tissue is lost from the wound area. This leads to the development of scars, which may be hyperplastic and disfiguring and lead to impaired body function.

Scars arise from the biological response of adult connective tissue to injury. Unlike foetal tissues which respond to incision or injury by regenerating new dermis to replace the lost/damaged tissue (i.e. bridging the defect with dermal collagen fibres with normal dermal collagen architecture) after birth, equivalent wounds are repaired rather than regenerated and the wound becomes filled with scar tissue. Thus the bridging tissue after birth does not replicate the original normal dermal architecture. During the repair process, fibroblasts (the cells which permeate all connective tissues and which synthesise the extra-cellular matrix including structural collagen) and small blood vessels migrate into the wound space to form highly cellular granulation tissue which transforms into the dense irregularly organised collagen mass described as scar tissue.

One solution to this particular tissue loss problem has been to apply three-dimensional collagen gels within the lost tissue area of the wound which subsequently acts as a matrix network for the growth of so-called histiotypic skin. The collagen used to form this particular gel is completely water-soluble and when it is applied, it is invaded with fibroblasts and small blood vessels, water is extruded and a fragile gel is formed in which the collagen molecule is polymerised to form collagen fibrils. Although reasonably successful in rebuilding the lost tissue in the area around the original wound, the initial three-dimensional matrix formed from the collagen gel does not replicate the normal matrix architecture of the body's natural tissue and, as such, the gel has no inherent stability. This inherent instability leads to the gel being rapidly re-absorbed by the body and replaced with scar-like tissue.

Other recent proposals to overcome the problem of scar tissue formation have involved the extremely difficult (and very expensive) use of monoclonal antibodies to suppress the action of growth factors such as transforming growth factor (TGF —β).

We have now surprisingly found that the favourable properties, including resistance to resorption, resistance to calcification, granulation and the ability to become recellularized and revascularised, which characterise the large scale structures disclosed in U.S. Pat. No. 5,397,353, are capable of being retained if the collagen material is presented in mouldable form at the fibre fragment level of organisation, where it can be used as a wound filler, or in injectable form for use in cosmetic and reconstructive surgery.

According broadly to the present invention there is provided an implant composition which comprises a biocompatible carrier medium having dispersed therein particles of collagenous material, where the particles comprise fragments of collagenous fibres and are thus sufficiently large to preserve the original architecture and molecular structure of the natural tissue material from which they are derived, and wherein the collagenous material is substantially free of non-fibrous tissue proteins, glycoproteins, cellular elements and lipids or lipid residues, and which is non-cytotoxic. Preferably, the material is free or substantially free of antigenic polysaccharides and mucopolysaccharides. The biocompatible medium may be, for example, a saline or dextran or hyaluronic acid solution.

Such compositions may vary widely in consistency. For example, if the particle size and concentration in the biocompatible medium is such as to produce a fairly liquid suspension, this can be injectable provided the particles are not too large. More concentrated thicker consistency compositions may be used as pasty wound filling compositions.

Such materials may be prepared from collagenous materials of human or animal origin, the preferred starting material being pig dermis, by methods as disclosed in U.S. Pat. No. 5,397,353 or analogously thereto. Depending on the starting material, the composition may contain a proportion of elastin. It is then possible, provided care is taken, to reduce the material from large pieces to small particles which can then be formulated into a sterile injectable composition or a sterile wound filling paste.

In order to produce a collagen paste with appropriate density and rheological properties (flow rate and an ability to retain shape after moulding), a suspension of collagenous particles in a suitable carrier can be prepared to form a controllable concentration of the composition.

Care must however be taken to ensure that the size reduction of the starting material is not accompanied by degradation of the molecular structure of the original material. The preferred method of providing particles of an appropriate size is by grinding or milling and this is preferably carried out in a ball or hammer mill which may be cooled to an appropriate temperature. Milling may be carried out in dry form (less than 10% moisture content) or in frozen hydrated form (20–80% moisture content).

Collagen which has been milled in a frozen hydrated state may be dehydrated by acetone extraction, freeze drying or in a current of air. The dry collagen powder may be suspended in an essentially non-aqueous, non-toxic, bio-compatible medium, such as for example, glycerol prior to injection.

An anaesthetic as for example, lignocaine may be incorporated into the composition.

The collagenous material may be, if desired, crosslinked, e.g. using a diisocyanate, in order to make it resistant to collagenolytic enzymes and thus render it substantially non-resorbable.

The preferred method of rendering the compositions sterile is by gamma irradiation.

The preferred particle size of the particles of collagenous material in the injectable compositions according to the present invention is from 50 to 500 microns. The particle size distribution may vary but preferably at least 50% of the particles are within +35% of the average particle size. The concentration of solids in the injectable composition is preferably in the range of 10 to 70% (w/v). In contrast, in the pasty wound filling compositions, the concentration of solids is generally up to 80%.

The efficacy of the compositions of the invention can be seen in vitro. It has been observed that when dispersed collagen fibre fragments (milled collagen) are seeded with human or rodent fibroblasts in tissue culture, the fibroblasts attach to the collagen fragments and aggregate them to form dense tissue like discs which are easily manipulable.

Furthermore, when injected in vivo, milled collagen is rapidly invaded by fibroblasts and small blood vessels (much more rapidly than collagen sheets) to form a new tissue in which the collagen fibre fragments are organised into intermeshing collagen fibres similar to normal dermal collagen architecture, i.e. are not resorbed and do not form scar tissue.

The injectable compositions can be used in a variety of clinical situations. For example, to control urinary incontinence and more specifically in intrinsic sphincter deficiency, by peri-urethral injection to reduce lumen aperture. Cosmetic applications include the use of injection of collagenous suspensions following eyebrow uplift, for lip augmentation and to rectify facial defects, frown lines and acne scars. As another example, in arthritic joints, there is often a marked loss and damage of the smooth cartilage layer which consists of chrondrocytes supported by a fibrous collagen matrix. There is evidence that under the inflammatory conditions in arthritic joints that collagenase is produced which destroys the collagen matrix of the cartilage layer. If a collagenous suspension according to the invention is injected into the joint, it may assist in producing a collagenase resistant matrix to support chrondrocytes and so repair the damage.

An alternative clinical scenario is where it is necessary to treat a large area of skin, for example, the back of the hand or neck in elderly patients where the skin has become very thin. A multi-point injection system may be employed for this purpose. Such a system may combine a number of needles mounted in a hollow block of metal or plastics material, the inlet of which is fed with collagenous suspension with a syringe, metering pump, piston peristaltic pump or any other suitable device.

The collagenous compositions of the invention may also be used for the purpose of supressing scar formation in surgical wounds, the milled collagenous material again serving to introduce fibre-structured fragments into the wound space immediately during or after closing the wound by suture or tape. Although totally against convention, such a procedure has been shown to be extremely beneficial. The introduction of the collagenous material fragments into newly-formed wounds, e.g. incisional spaces, provides an anatomically "thin" matrix of collagen-rich sites for the fibroblasts and small blood vessels to migrate in to from the wound edges. This has a profound influence on the behaviour of the fibroblasts as within such a collagen-rich environment within the wound space, they do not receive the signals to produce granulation tissue and synthesise excess new collagen. In other words scar formation is largely suppressed. This simple "mechanical" approach differs from the prior art, in particular the use of monoclonal antibodies as it is far simpler to apply and far cheaper.

Use of milled collagen by injection through fine needles is somewhat limited because of the mode of introduction of collagenous material to the site where it is needed. However, the thicker consistency compositions, which allow the use of a wider spectrum of collagenous material fragment sizes, can be used in a variety of situations where an injectable material would not be suitable. Thus in the treatment of more extensive or severe wounds, in order to replace lost tissue and to greatly reduce the formation of scar tissue, collagen fibre fragments may be introduced as a pasty composition into the wound space before applying an appropriate dressing or closure by suture or tape. For example, the composition may be used for immediate reconstruction following breast lumpectomy. For skin-loss defects, including those following traumatic chemical or burn injury, or those presented by leg ulcers, the pasty composition may be used to replace lost dermis with appropriate cover and dressing.

The following examples will serve to illustrate the invention:

EXAMPLE 1

Under sterile conditions, samples of porcine dermal collagen were cut into small pieces (1 to 3 mm$^3$) and dehydrated using several changes of 100% ethanol and anhydrous acetone. Using a ball mill, the dried collagen pieces were ground and sieved to produce a fine white powder. The sieved powdered collagen was rehydrated in s sterile phosphate buffered saline to produce a collagen suspension concentration of 60 to 70% (w/v).

EXAMPLE 2

Small pieces of blotted porcine collagen were frozen in liquid nitrogen and ground in a cryogenic mill. The ground collagen fragments were suspended in sterile phosphate buffered saline to produce a collagen suspension concentration of 60 to 70% (w/v).

EXAMPLE 3

To directly examine cell/collagen biointeraction, sieved powdered porcine dermal collagen was rehydrated in complete mammalian cell culture medium to produce a collagen suspension concentration of 70% (w/v) and seeded with either primary human foreskin fibroblasts or primary rat skin dermal fibroblasts.

Collagen/fibroblast samples were aliquoted into COSTAR® a registered trademark in relation to cell culture wells and incubated at 37° C., 5 to 7% (w/v) $CO_2$ saturated humidity. As studied over a 21 day incubation period, both human and rat fibroblasts proliferated and migrated into and adhered to the porcine collagen fragments which they assembled into densely packed clumps or discs.

EXAMPLE 4

To examine in vivo performance collagen suspensions were injected (0.2 ml/injection through a 21 gauge needle intracutaneously into dorsal sites in isogenic PVG/Ola rats. Sequential biopsies up to 12 month post injection showed the persisting macroscopic presence of injected collagen as subdermally located white discs with no overt signs of loss of injected collagen mass nor of adverse host reactions. Early biopsies showed that the injected collagen remains in situ and within 9 days is fully invaded with fibroblasts and small blood vessels. Subsequent histology showed that the collagen fibre fragments are organised into intermeshing collagen fibres to produce a tissue with an architecture resembling normal dermal collagen.

EXAMPLE 5

Under sterile conditions, samples of porcine dermal collagen produced in accordance with the process described in U.S. Pat. No. 5,397,353 were cut into small pieces (1 to 3 $mm^3$), frozen in liquid nitrogen and ground in a cryogenic mill. The ground collagen fragments were suspended in sterile phosphate buffered saline to produce a pasty composition with a solids content of 80% w/v.

EXAMPLE 6

Pockets were made in the skin of the pinnae of PG/Ola rats, the collagen paste composition inserted with a spatula and the wounds closed and secured with a spray dressing. Sites of collagen insertion were biopsied at monthly intervals for histological examination. Over a period of 6 months, the collagen implants which persisted as raised skin bumps, became incorporated into surrounding host tissues and no adverse effects were found.

EXAMPLE 7

1 ml of the collagen paste was injected by "trocar" or large bore needle subdermally in the dorsum of PVG/Ola rats. This "soft tissue filler" persisted with no adverse host reactions over a period of six months.

EXAMPLE 8

Full-thickness incisional skin wounds were made in the dorsum of PVG/Ola rats. The wounds were closed using interrupted sutures and a suspension of collagen composition was injected into the wounds until it extruded above the wound surface. Wounds were biopsied at 6, 8, 10 and 14 days for histological examination which revealed evidence of incisional healing in the absence of observable scar tissue.

EXAMPLE 9

The collagen paste composition, with or without prior seeding with isogenic fibroblasts in culture, was used to fill 1×1 cm full-thickness excised skin wounds in PVG/Ola rats and covered with a semi-permeable membrane (Opsite—REGISTERED TRADE MARK) as a primary dressing. Subsequent observation and histology revealed that the implanted collagen composition becomes covered by migrating epithelium from the wound margins within 28 days and acts as an effective and persisting dermal replacement.

What is claimed is:

1. An implant composition comprising a biocompatible carrier medium having dispersed therein solid or semi-solid particles of collagenous material that are derived from a natural tissue material,
   wherein said collagenous material preserves the original fiber architecture and molecular ultrastructure of the natural tissue material from which it is derived,
   wherein said collagenous material is substantially free of non-fibrous tissue proteins, glycoproteins, cellular elements, lipids or lipid residues,
   wherein said collagenous material is non-cytotoxic,
   wherein said implant composition is capable of use as a component of a paste, gel or an injectable solution, and
   wherein said particles of collagenous material have a particle size within the range of approximately 50 microns to approximately 500 microns.

2. The implant composition of claim 1, wherein said particles of collagenous material have a particle size distribution wherein the particle sizes of at least 50 percent of the particles are within 35 percent of the average particle size.

3. The implant composition according to claim 1, wherein said collagenous material is free of antigenic polysaccharides and mucopolysaccharides.

4. The implant composition according to claim 1, wherein said collagenous material is substantially free of antigenic polysaccharides and mucopolysaccharides.

5. The implant composition according to claim 1, wherein said collagenous material contains a proportion of elastin.

6. The implant composition of claim 1, wherein said collagenous material is cross-linked.

7. The implant composition of claim 1, wherein said biocompatible carrier medium is at least one of saline, glycerol, a dextran solution, a non-toxic antigenic viscous polysaccharide.

8. The implant composition of claim 1, wherein said collagenous material comprises approximately 10 percent by weight to approximately 90 percent by weight of the implant composition.

9. The implant composition of claim 1, wherein said collagenous material comprises approximately 10 percent by weight to approximately 80 percent by weight of the implant composition.

10. The implant composition of claim 1, wherein said collagenous material comprises approximately 10 percent by weight to approximately 70 percent by weight of the implant composition.

11. The implant composition of claim 1, wherein said composition is moldable or shapeable.

12. The implant composition of claim 1 for use as part of a medical, surgical, reconstructive or cosmetic treatment or procedure.

13. The implant composition of claim 1 for prevention or suppression of scar formation.

* * * * *